United States Patent [19]

Steffensmeier

[11] Patent Number: 4,732,141

[45] Date of Patent: Mar. 22, 1988

[54] CHIROPRACTIC TABLE WITH SWINGABLE SECTION

[76] Inventor: Lloyd A. Steffensmeier, 102-122 West Main St., Lisbon, Iowa 52253

[21] Appl. No.: 912,008

[22] Filed: Sep. 25, 1986

[51] Int. Cl.[4] ............................ A61F 5/00; A61F 5/04

[52] U.S. Cl. .......................................... 128/74; 128/70

[58] Field of Search ........................ 128/74, 73, 72, 71, 128/70, 69, 68

[56] References Cited

U.S. PATENT DOCUMENTS

| | | | |
|---|---|---|---|
| 1,113,658 | 10/1914 | Landenberger | 128/74 |
| 1,190,195 | 7/1916 | Schmidt | 128/74 |
| 1,417,675 | 5/1922 | McManis | 128/74 |
| 1,602,196 | 10/1926 | Iverson et al. | 128/70 |
| 1,686,979 | 10/1928 | McManis | 128/70 |
| 3,092,102 | 6/1963 | Thompson | 128/70 |
| 4,569,339 | 2/1986 | Barnes | 128/74 |
| 4,649,905 | 3/1987 | Barnes | 128/74 |
| 4,655,200 | 4/1987 | Knight | 128/71 |
| 4,660,549 | 4/1987 | Kowalski et al. | 128/69 |

*Primary Examiner*—Edgar S. Burr
*Assistant Examiner*—Tonya Lamb
*Attorney, Agent, or Firm*—James C. Nemmers

[57] ABSTRACT

A chiropractic table having a feature that facilitates the treatment of rotatory scoliosis and scoliosis of the spine. The chest-lumbar section of the table is mounted so that it can both pivot and slide thus producing a swinging movement about a central pivot point located above the longitudinal axis of the table. This type of movement is beneficial in the treatment of scoliosis. The mounting structure of the chest-lumbar section is such that the section can be raised or lowered to accommodate the particular anatomy of the patient and also provides for inclusion in the section of the drop feature used in the treatment of scoliosis and other conditions.

6 Claims, 6 Drawing Figures

FIG 4
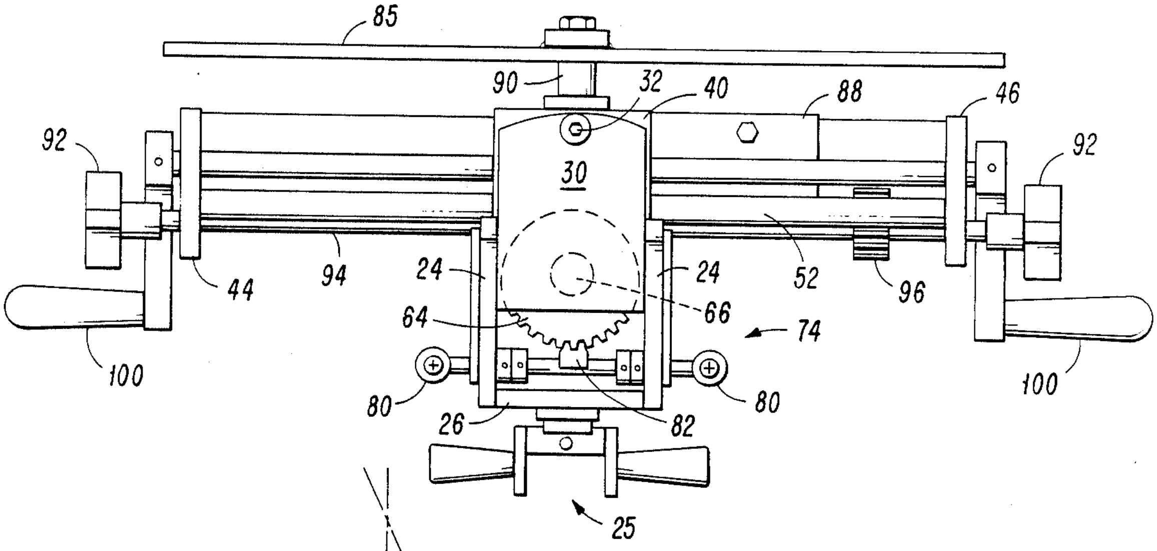
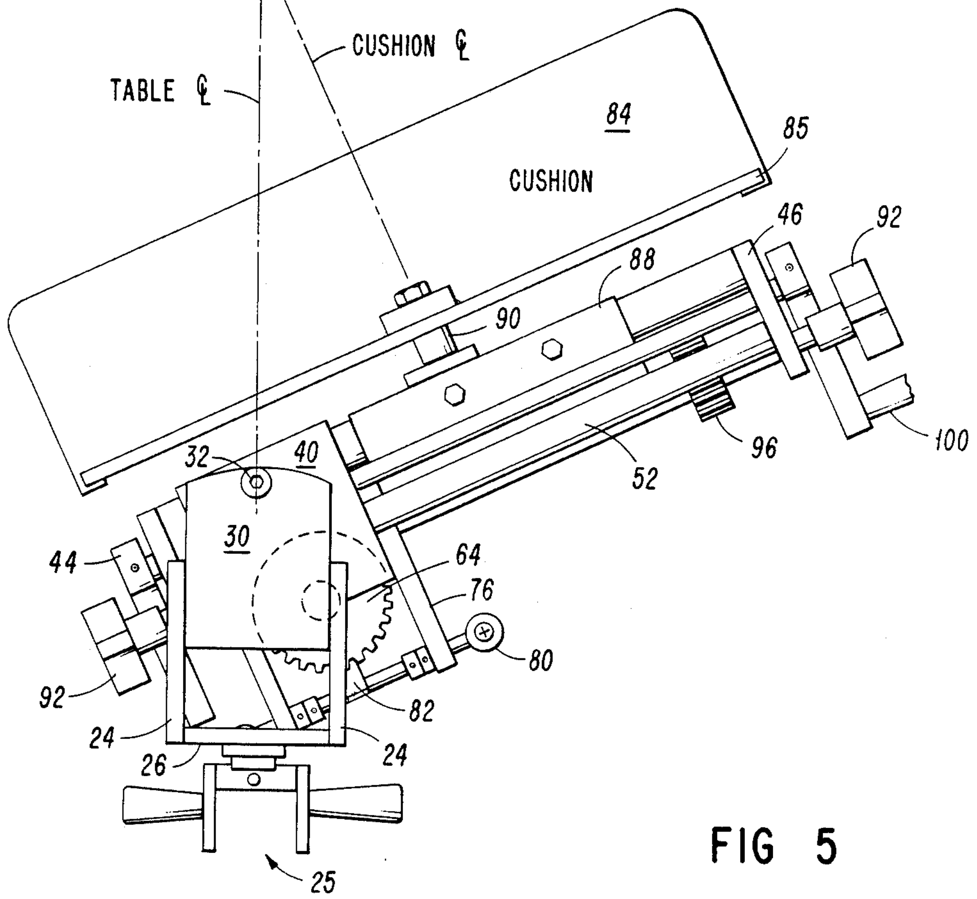
FIG 5

CHIROPRACTIC TABLE WITH SWINGABLE SECTION

BACKGROUND OF THE INVENTION

One of the conditions treatable by chiropractic medicine is scoliosis of the spine. In the condition of rotatory scoliosis, the spine is not only curved so as to be out of alignment but it is also twisted about its axis. There are well known procedures for treating this condition using chiropractic medicine. A specially designed table is preferably used in which the chest-lumbar section of the table can be tilted sideways of the table to aid the practitioner in performing the proper procedure for treatment of this condition. The support and mounting mechanism for the chest-lumbar section of the table must be constructed so that the spine stays substantially centered on the table as the section swings sideways. This requires that the pivot center of the section be above the longitudinal axis of the table.

Known mechanisms for allowing the chest-lumbar section of the table to properly swing sideways are relatively simple, but are such that the section of the table cannot be adjusted vertically to accommodate the particular anatomy of the patient. Moreover, a common chiropractic procedure for certain conditions, including scoliosis, is to provide a table with a drop feature which permits the practitioner to raise the section of the table slightly, cock it and then apply pressure to the patient's spine until a predetermined amount of pressure is reached at which time the section of the table will drop producing the desired effect. With known designs of tables, there is no supporting and mounting structure that will allow proper swinging of the section for the treatment of scoliosis while still allowing the height of the section to be vertically adjusted and the drop feature to be included. The ability to provide all three features in a single section in a single table allows the practitioner to use a single table for all procedures. If a patient requires both treatments, this eliminates having to move the patient to a different table perhaps in a different treatment room. It also is very cost effective and will allow the practitioner to acquire a single table that can be used for a variety of procedures.

SUMMARY OF THE INVENTION

The invention provides a supporting and mounting structure for a chest-lumbar section in which the section is supported so that it can be swung sideways about a pivot point located above the longitudinal axis of the table thereby maintaining the axis of the spine substantially centered on the table at all times regardless of the position to which the chest-lumbar section is moved. This is accomplished by a unique supporting structure in which a multiple gear-rack arrangement is provided with one rack stationary and the other rack secured to the underside of the cushion. These racks engage gears of different sizes both mounted on a single axis that is not a fixed axis. The section of the table to which the cushion is attached contains rods that slide in blocks that are pivotally mounted about a fixed pivot. Thus as the cushion is swung from one position to another, the rods slide through the pivotally mounted blocks and provide a motion that is a swinging motion about a pivot that is above the table thus maintaining the spine of the patient substantially centered on the table as the section is swong. The gear-rack arrangement also permits a simple locking mechanism to be used to lock the cushion in a selected position. Also, because the entire supporting structure for the cushion moves, the cushion supporting the patient can be raised and lowered and the drop feature can be incorporated into the section.

BRIEF DESCRIPTION OF THE DRAWINGS

FIG. 4 is an end view of the chest-lumbar section showing the section locked into position with the section level;

FIG. 5 is an end view similar to FIG. 4 but showing the section swung to the right.

DESCRIPTION OF THE PREFERRED EMBODIMENT OF THE INVENTION

Figure 1:
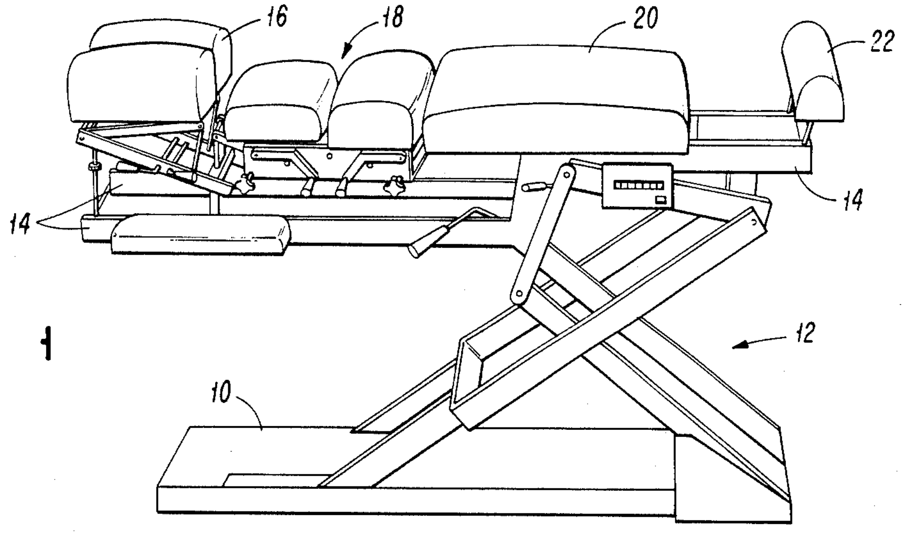
FIG. 1 is a perspective view of a typical chiropractic table of multiple sections and of the type to which the invention relates.
Figure 2:
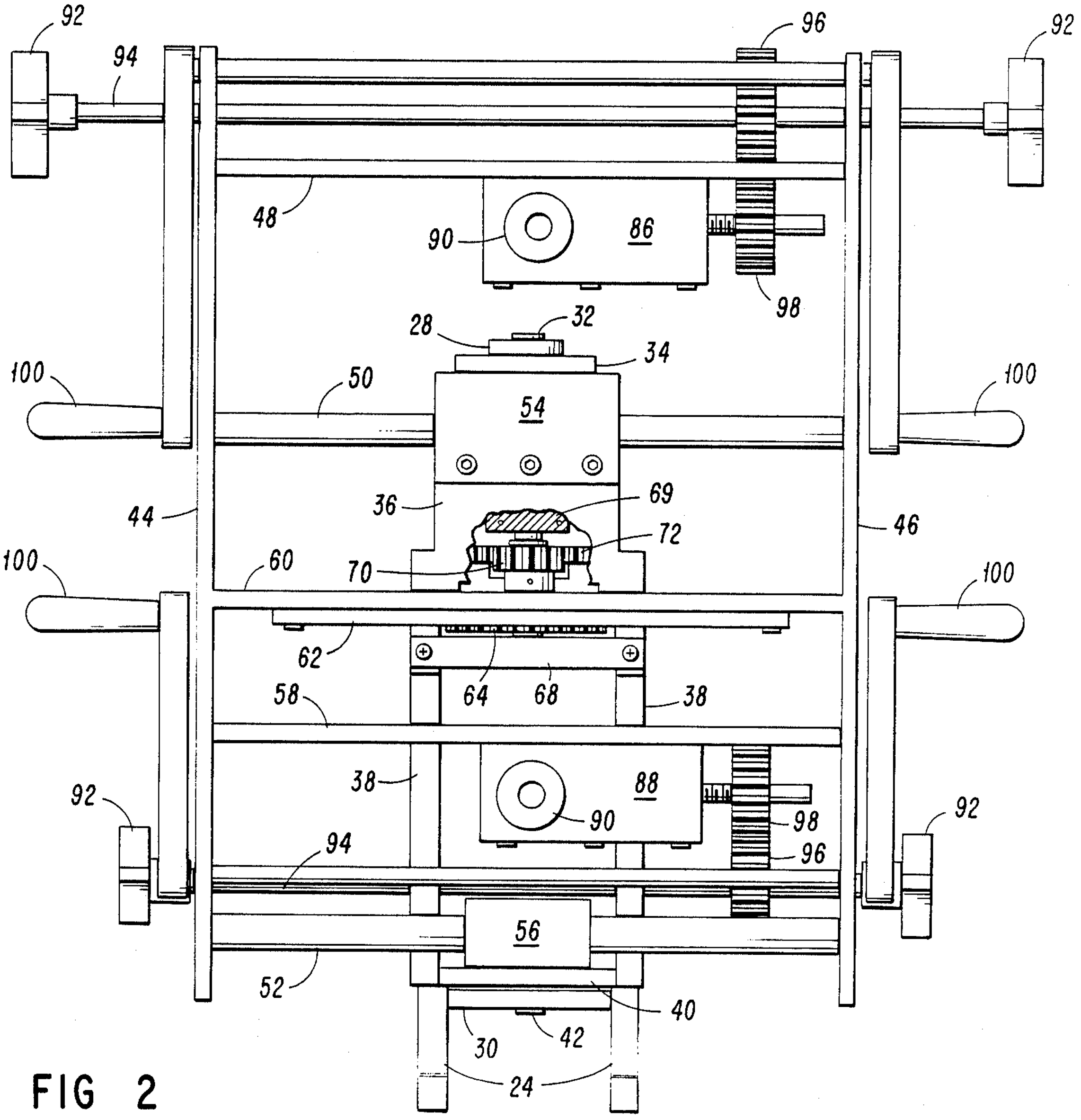
FIG. 2 is a top plan view of the chest-lumbar section of the table with some parts broken away to more clearly illustrate the invention.
Figure 3:
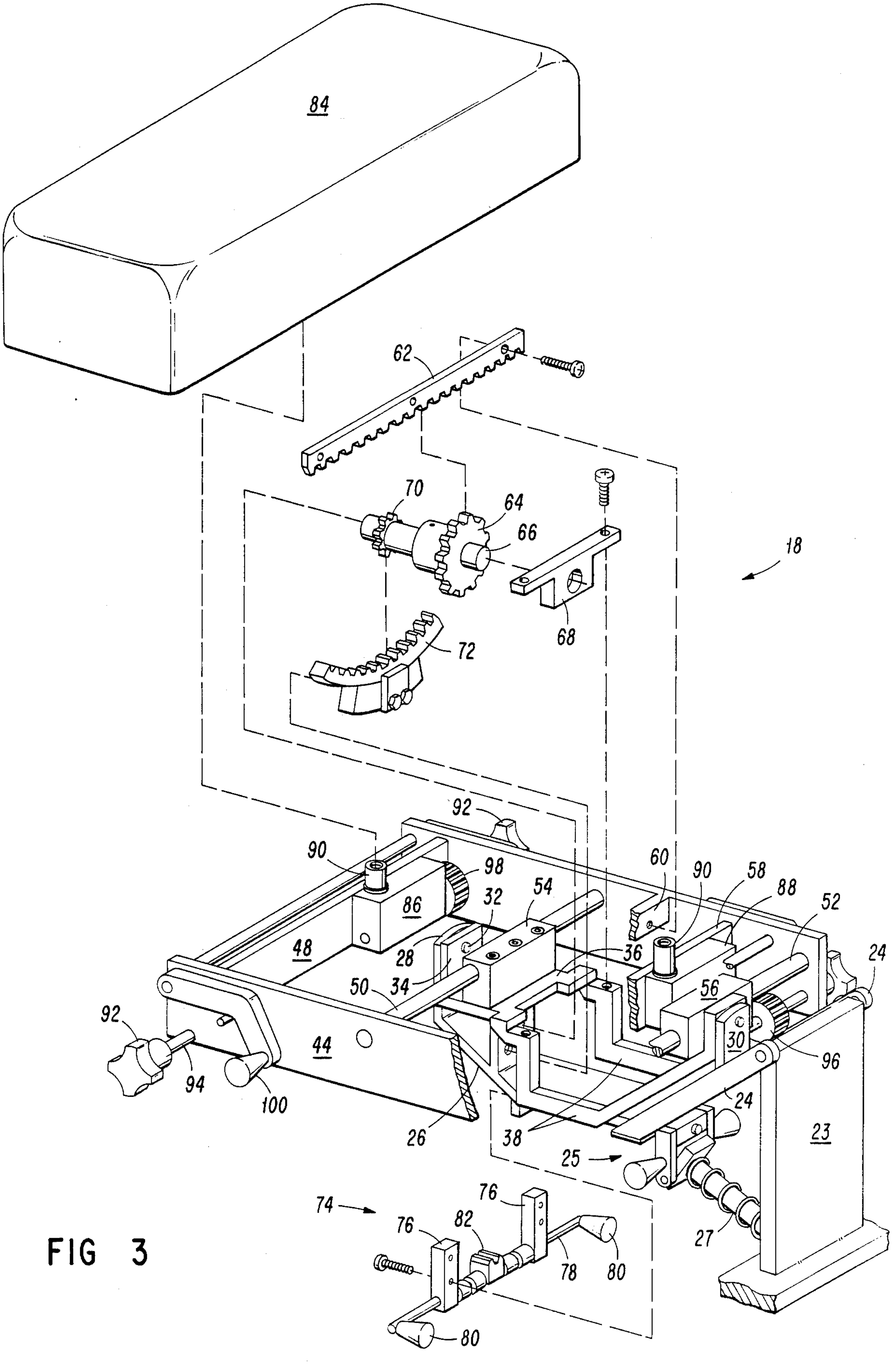
FIG. 3 is an exploded view of the chest-lumbar section with parts also broken away.
Figure 6:
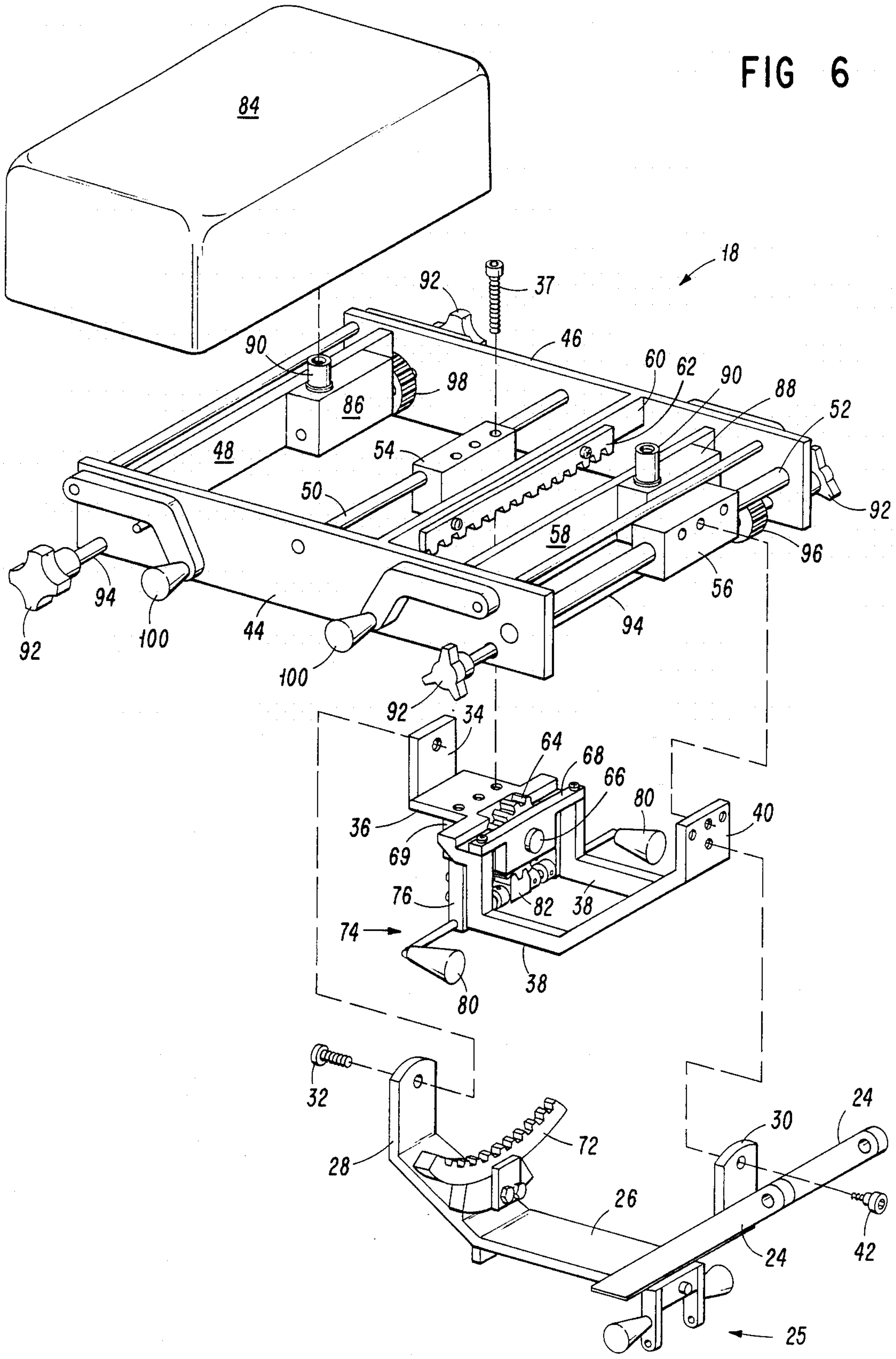
FIG. 6 is an exploded view of the chest-lumbar section similar to FIG. 3 but showing the components in subassemblies.

In FIG. 1, there is illustrated a chiropractic table of a conventional type that includes a base 10 and supporting framework 12 that has cushion supporting main members 14 that extend generally horizontally. At one end of the frame 14 there are mounted for independent movement a pair of head cushions 16 adjacent to which is a chest-lumbar section indicated generally by the reference numeral 18. FIGS. 2–6, especially FIG. 3 and FIG. 6, illustrate in detail the chest-lumbar section to which the invention relates. Althouogh FIG. 1 views the table as if a person were standing on the left side of the table, FIGS. 3 and 6 are viewed as if a person were standing at the right front of the table and looking at an exploded view of the chest-lumbar section of the table. Also mounted independently on frame members 14 is a pelvic section 20 and foot and ankle rest 22 which are at the end of the table sometimes referred to herein as the rear end. As is well known, each of the various sections of the chiropractic table are mounted for movement independently of each other so that each section can be adjusted to the desired height and angle in order to carry out the desired chiropractic procedure.

As previously indicated, the invention relates primarily to the chest-lumbar section 18 and the manner in which it is supported on the frame members 14. However, the principles of the invention could be applied to any section of the table as well if the particular movement provided by the invention is to be used in a particular chiropractic procedure. The invention thus relates to the mounting and supporting structure for one of the independently moveable sections of the chiropractic table. Otherwise, the chiropractic table would be any standard known chiropractic table of which there are many different designs and types. Referring now to FIGS. 2–5, there is shown in these figures the chest-lumbar section 18 in detail. The chest-lumbar section 18 is affixed to the frame members 14 in any suitable manner such as by a pair of support arms 24 pivotally mounted on vertical support 23 that is affixed to frame members 14. Locking means 25 provides for attaching the section 18 to a lower support arm 27 (as shown in FIG. 3) so that the entire section 18 is thus supported at its head end in a manner well known to those skilled in the art. Support arms 24 and 27 may provide, if desired, for pivotal movement of the entire section 18 about a horizontal axis transverse to the longitudinal axis of the tablel itself. Such movement does not form a part of the invention but does illustrate that the mounting structure of the invention permits such movement where desired.

As best seen in FIG. 6, support arms 24 are attached to a supporting frame 26 which has vertically upstanding pivot supports 28 and 30 which are spaced-apart along the longitudinal axis of the table. The footward or rear pivot support 28 is pivotally connected by pin 32 to the upstanding leg 34 of a support member the other leg 36 of which extends forewardly. At the forward end of leg 36 the support is bifurcated with transversely spaced-apart arms 38 extending forewardly to an upstanding portion 40 that is connected by pivot pin 42 to the head or forward pivot support 30. Thus, the framework that is comprised of members 34, 36, 38 and 40 provide a "cradle" that pivots about pivot pins 32 and 42 on the pivot supports 28 and 30 respectively. This "cradle" provides the support for the chest-lumbar cushion 84 as described hereinafter.

Since the purpose of the invention is to provide not only for pivotal movement of the chest-lumbar cushion 84 but also swingable sideways movement so that the spine of the patient resting on the table will remain substantially centered on the table, the cradle construction must also be combined with the mounting structure for the chest-lumbar section in a manner that will provide for such swingable movement.

The main supporting framework for the chest-lumbar cushion 84 consists of side members 44 and 46 joined by a rear end member 48 and a middle cross bar 50 and a forward cross bar 52 each of which extends transversely between the side members 44 and 46 and is rigidly connected to these members. This framework is open in the center so as to receive the cradle construction previously described. The cross rods 50 and 52 extend through pillow blocks 54 and 56 which are attached to the support structure of the cradle, pillow block 54 being attached to the arm 36 by fasteners 37 while pillow block 56 is attached to the upstanding member 40 by fastener 42. A transverse member 58 extends between the side members 44 and 46 between the cross rods 50 and 52. Also, a cross support 60 extends between the side members 44 and 46. Affixed to cross member 60 is a rack 62 which engages a large spur gear 64 turnable on shaft 66 which has one end support in a bearing member 68 that is affixed to the upper portions of arms 38 just to the rear of the arm 36. The other end of shaft 66 is supported in bearing member 69 (FIG. 2) and contains a small spur gear 70 that engages an arcuate rack 72 that is affixed rigidly to the frame 26 that is in turn pivotally connected to the table through the arms 24 as previously described. Thus, as the cradle framework pivots about the pivot pins 32 and 42, the cushion supporting framework will slide transversely on cross rods 50 and 52 carrying with it the rack 62 which will in turn rotate the large spur gear 64 and small spur gear 70 which will follow the arc of the arcuate spur gear 72. Engagement of small spur gear 70 with the arcuate rack 72 provides a controlled track for the swingable movement of the cushion framework, and the rack-gear arrangement also provides for locking of the cushion framework in a selected position. This is accomplished by a locking mechanism indicated generally by the reference numeral 74 (FIG. 3). This mechanism consists of a pair of upright supports 76 affixed to the framework 38 with a shaft 78 extending through the supports 76. Shaft 78 has a pair of control knobs 80 at each of its outer ends so that the locking mechanism can be operated from either side of the table. Shaft 78 has eccentrically mounted at its center locking teeth 82. Since the locking mechanism 74 is positioned on framework 38 just beneath the large spur gear 64, grasping of a knob 80 and rotating shaft 78 counterclockwise will raise the locking teeth 82 so that they engage the teeth of the spur gear 64 thus preventing its further movement. Engagement of the locking mechanism is best seen in FIG. 4 and FIG. 6.

Each patient support cushion 84 is affixed to a support plate 85 and is mounted in the following manner so that it is supported by the framework but is also moveable vertically independently of it. A drop control and vertical lifting mechanism 86 is secured to the end member 48 of the cushion supporting framework. Similarly, a vertical lifting and drop mechanism 88 is secured to the cross member 58. Each mechanism 86 and 88 contains a vertically moveable rod 90 which rods 90 support the cushions 84. There is only one cushion 84 shown in FIG. 3, but as illustrated in FIG. 1, there are two such cushions which are independently moveable vertically of the other but which are both moveable with the cushion supporting framework previously described. Cushions 84 are not shown in FIGS. 4 and 5, but the supporting plates 85 are shown. Tension adjusting knobs 92 are provided on each side of the table for each of the lifting and drop mechanisms 86 and 88. Knobs 92 are mounted on shafts 94 which when turned turn a spur gear 96 which in turn rotates a second gear 98 that through the mechanisms 86 and 88 respectively will vary the resistance on a spring-loaded detent (not shown) on the vertical rods 90 thus varying the resistance in raising and lowering cushions 84. Also built into the mechanisms 86 and 88 are features that are known and commercially used to provide a drop technique used by the practitioner. This drop technique employs cocking arms 100 which allow the cushions 84 to be individually raised, and when pressure is applied to a patient resting on a cushion 84, the cushion will abruptly drop when a predetermined amount of pressure is applied. However, the drop is a predetermined limited distance. The raising and lowering and drop features are well known to those skilled in the art, have been used commercially for years and do not form a part of the invention. However, they are illustrated to show their relationship to the tilting and pivoting mechanism of the invention which permits these features to be employed in a single table with the tilting-pivoting mechanism that is used for the scoliosis procedure.

Although the operation of the swingable mounting construction should be evident from the foregoing description, it is briefly summarized as follows. Assuming that the chest-lumbar section is in the position shown in FIG. 4 with the cushion 84 substantially horizontal, the practitioner would disengage the locking teeth 82 from the spur gear 64 by rotating the handles 80 downwardly. The chest-lumbar section 18, including both cushions 84, can then be swung sideways to the desired position, and the locking mechanism 74 again used to engage the locking teeth 82 into the spur gear 64 to maintain the section in its desired selected position. As the chest-lumbar section 18 is swung sideways, the rack 62 will ride on spur gear 64 rotating small spur gear 70 and moving it along the arcuate rack 72. Since the rack 62 is affixed to the cross member 60, and because the shaft 66 supporting spur gears 64 and 70 is turnable in the blocks 68 and 69 affixed to the frame arms 36 and 38 of the cradle mechanism, the cradle mechanism will rotate about pivot pins 32 and 42 and the cross rods 50 and 52 will slide through the pillow blocks 54 and 56. FIG. 5 illustrates the chest-lumbar section 18 swung to the right to its limit. In this position, and with a patient on the cushions 84 (cushions 84 are not shown in FIGS. 4 and 5), the patient's spine would be located substantially centered above the fixed pivot points 32 and 42. Thus, regardless of the position of the chest-lumbar section 18, the patient's spine would remain substantially centered on the table.

Furthermore, note that the mounting and supporting structure for the swinging movement in no way interferes with the independent operation of each of the cushions 84, each of which can be raised or lowered independently and each of which can be utilized for a drop procedure.

Having thus described the invention in connection with the preferred embodiment thereof, it will be evident to those skilled in the art that various revisions and modifications can be made to the preferred embodiment without departing from the spirit and scope of the invention. It is my intention however that all such revisions and modifications as are obvious to those skilled in the art will be included within the scope of the following claims.

What is claimed is:

1. In a chiropractic table having a base and framework for supporting multiple independent sections that include a chest-lumbar section, a pelvic section and head and foot sections spaced longitudinally along the table, a supporting structure for one of the sections comprising a main frame connectable to the supporting framework of the table and providing first and second pivots spaced longitudinally of the table which pivots provide for pivotal connection along a horizontal longitudinal axis, a cradle assembly pivotally mounted on said first and second pivots, patient supporting means including a framework operatively connected to the cradle assembly so as to provide for limited movement of the patient supporting means relative to the cradle assembly and transversely of the table, said patient supporting means also including a patient engaging member controllably moveable vertically within a limited distance relative to the framework for the patient supporting means, and locking means to maintain the patient supporting means and cradle assembly in a selected stationery position.

2. In the chiropractic table of claim 1 in which the connection between the framework of the patient supporting means and the cradle assembly provides for sliding movement transversely of the table.

3. In the chiropractic table of claim 2 in which the framework of the patient supporting means includes a pair of rods spaced-apart longitudinally of the table and extending transversely of the table, and the cradle assembly includes a pair of pillow blocks spaced-apart longitudinally so as to receive through them said rods, thereby providing for slideable movement between the framework of the patient supporting means and the cradle assembly.

4. In the chiropractic table of claim 3 in which there is affixed to the main frame an arcuate rack, the cradle assembly supports a shaft rotatable about a horizontal longitudinal axis and containing a pair of gears, one of said gears engaging the arcuate rack, and a second rack is affixed to the patient engaging member so as to be engagable with the second gear, said gear and rack arrangement providing for controlled pivotal movement of the cradle assembly relative to the main frame and controlled slideable movement of the patient supporting means relative to the cradle assembly.

5. In the chiropractic table of claim 4 in which the locking means is secured to the main frame and includes a locking member selectively moveable into and out of engagement with one of the gears of the gear-rack assembly to prevent said gears from rotating.

6. In the chiropractic table of claim 5 in which the framework of the patient supporting means includes a drop mechanism for controlling the relative vertical movement of the patient engaging member relative to the framework of the patient supporting means.

* * * * *